(12) United States Patent
Anglada et al.

(10) Patent No.: US 8,338,436 B2
(45) Date of Patent: Dec. 25, 2012

(54) **AMORPHOUS FORM OF N-{2-FLUORO-5-[3-(THIOPHENE-2-CARBONYL)-PYRAZOLO[1,5-*A*]PYRIMIDIN-7-YL]-PHENYL}-N-METHYL-ACETAMIDE**

(75) Inventors: Luis Anglada, Barcelona (ES); Albert Palomer, Barcelona (ES); Antonio Guglietta, Barcelona (ES)

(73) Assignee: Ferrer International, S.A., Barcelona (ES)

( * ) Notice: Subject to any disclaimer, the term of this patent is extended or adjusted under 35 U.S.C. 154(b) by 423 days.

(21) Appl. No.: 12/513,884

(22) PCT Filed: Nov. 7, 2007

(86) PCT No.: PCT/EP2007/062014
§ 371 (c)(1),
(2), (4) Date: Jan. 28, 2010

(87) PCT Pub. No.: WO2008/055934
PCT Pub. Date: May 15, 2008

(65) Prior Publication Data
US 2010/0137339 A1    Jun. 3, 2010

Related U.S. Application Data

(60) Provisional application No. 60/864,814, filed on Nov. 8, 2006.

(30) Foreign Application Priority Data

Nov. 8, 2006    (EP) ..................................... 06123652

(51) Int. Cl.
*A01N 43/90* (2006.01)
*A61K 31/519* (2006.01)
*C07D 487/00* (2006.01)

(52) U.S. Cl. ..................................... 514/259.3; 544/281

(58) Field of Classification Search ........................ None
See application file for complete search history.

(56) References Cited

U.S. PATENT DOCUMENTS

| | | | |
|---|---|---|---|
| 4,521,422 A | 6/1985 | Dusza et al. | |
| 6,399,621 B1 | 6/2002 | Dusza et al. | |
| 2006/0063784 A1 | 3/2006 | Wang et al. | |
| 2006/0063785 A1 | 3/2006 | Wang et al. | |
| 2006/0189633 A1 | 8/2006 | Huang et al. | |

FOREIGN PATENT DOCUMENTS

| | | |
|---|---|---|
| WO | WO-2005/014597 A1 | 2/2005 |
| WO | WO-2006/136530 A1 | 12/2006 |
| WO | WO2006136530 * | 12/2006 |

OTHER PUBLICATIONS http://www.britannica.com/EBchecked/topic/553257/solid, last accessed on Mar. 23, 23012.*
Final Office Action dated Apr. 14, 2011 issued in U.S. Appl. No. 11/922,602.
International Search Report issued in PCT/EP2006/063243 on Sep. 28, 2006.
Non-Final Office Action dated Dec. 9, 2010 issued in U.S. Appl. No. 11/922,602.

* cited by examiner

*Primary Examiner* — Jeffrey Murray
(74) *Attorney, Agent, or Firm* — Birch, Stewart, Kolasch & Birch, LLP

(57) ABSTRACT

The present invention relates to an amorphous form of N-{2-Fluoro-5-[3-(thiophene-2-carbonyl)-pyrazolo[1,5-a]pyrimidin-7-yl]-phenyl}-N-methyl-acetamide, methods for its preparation, its use as a therapeutically active agent and pharmaceutical compositions comprising the novel form.

8 Claims, 4 Drawing Sheets

AMORPHOUS FORM OF N-{2-FLUORO-5-[3-(THIOPHENE-2-CARBONYL)-PYRAZOLO[1,5-A]PYRIMIDIN-7-YL]-PHENYL}-N-METHYL-ACETAMIDE

This application is the National Phase of PCT/EP2007/062014 filed on Nov. 7, 2007, which claims priority under 35 U.S.C. 119(e) to U.S. Provisional Application No. 60/864,814 filed on Nov. 8, 2006, and under 35 U.S.C. 119(a) to patent application Ser. No. EP 06123652.7 filed in Europe on Nov. 8, 2006, all of which are hereby expressly incorporated by reference into the present application.

The present invention relates to an amorphous form of N-{2-Fluoro-5-[3-(thiophene-2-carbonyl)-pyrazolo[1,5-a]pyrimidin-7-yl]-phenyl}-N-methyl-acetamide, methods for its preparation, its use as a therapeutically active agent and pharmaceutical compositions comprising the novel form.

N-{2-Fluoro-5-[3-(thiophene-2-carbonyl)-pyrazolo[1,5-a]pyrimidin-7-yl]phenyl}-N-methyl-acetamide is a potent ligand of $GABA_A$ (γ-aminobutyric acid$_A$) receptors useful in the treatment or prevention of anxiety, epilepsy, sleep disorders, and insomnia, for inducing sedation-hypnosis, anesthesia, and muscle relaxation, and for modulating the necessary time to induce sleep and its duration, such as described in PCT/EP2006/063243 and U.S. 60/692866.

Throughout the present application the term "compound (I)" refers to N-{2-Fluoro-5-[3-(thiophene-2-carbonyl)-pyrazolo[1,5-a]pyrimidin-7-yl]-phenyl}-N-methyl-acetamide.

The compound (I) reported in the above specifications is a crystalline material which shows a melting point of 165-167° C.

However, the use of compound (I) in crystalline form has been hampered by its physical characteristics, for instance its low solubility. In fact, crystalline form of compound (I) is very low soluble, which may affect its therapeutic applicability and also the manufacture of aqueous compositions thereof.

Clearly, any improvement in the physical characteristics of compound (I) would potentially offer a more beneficial therapy and enhanced manufacturing capabilities.

Thus, it would be a significant contribution to the art to provide solid amorphous of compound (I) which have increased solubility, methods for its preparation, its use as a therapeutically active agent and pharmaceutical compositions comprising the novel forms.

The present invention provides compound (I) in an amorphous form. Advantageously, solubility of the amorphous form is about twice as high as the one of crystalline product.

Conventional processes for the preparation of amorphous substances comprise melting said substances and rapidly cooling the melt. However, such methods usually are limited to scale laboratory because they are impractical and scarcely suitable for industrial use.

In another aspect the present invention further provides a process for the preparation of amorphous form which process comprises: (i) dissolving N-{2-Fluoro-5-[3-(thiophene-2-carbonyl)-pyrazolo[1,5-a]pyrimidin-7-yl]-phenyl}-N-methyl-acetamide in dichloromethane; (ii) evaporating the solvent under vacuum; and (iii) drying the product to remove residual solvent.

In a preferred embodiment the process of the present invention comprises:
  (i) dissolving N-{2-Fluoro-5-[3-(thiophene-2-carbonyl)-pyrazolo[1,5-a]pyrimidin-7-yl]-phenyl}-N-methyl-acetamide in dichloromethane;
  (ii) adding charcoal to the solution;
  (iii) warming the mixture to 30-50° C.;
  (iv) agitating the mixture for 20-45 minutes;
  (v) cooling the suspension to 15-30° C.;
  (vi) removing charcoal by filtration;
  (vii) evaporating the solvent under vacuum; and
  (viii) drying the product under vacuum at 40-60° C. to remove residual solvent.

In a preferred embodiment, the mixture in step (iii) is warmed to 40° C. (±5° C.).

In another embodiment, the mixture is agitated in step (iv) for 30 minutes (±5 minutes).

In still another embodiment, the suspension in step (v) is cooled to 20-25° C.

In still yet another embodiment, the product in step (viii) is dried at 50° C. (±5° C.).

Another aspect of the present invention is to provide the use of an amorphous form of compound (I) as a medicament.

Another aspect of the present invention is to provide a pharmaceutical composition comprising an amorphous form of compound (I) in admixture with one or more pharmaceutically acceptable carriers, excipients, diluents or adjuvants.

Another aspect of the present invention is to provide a pharmaceutical composition comprising an amorphous form of compound (I) for use in the treatment or prevention of anxiety, epilepsy, sleep disorders, and insomnia, for inducing sedation-hypnosis, anesthesia, and muscle relaxation, and for modulating the necessary time to induce sleep and its duration.

Pharmaceutical compositions include those suitable for oral, rectal and parenteral (including subcutaneous, intramuscular, and intravenous) administration, although the most suitable route will depend on the nature and severity of the condition being treated. The most preferred route of the present invention is the oral route. The compositions may be conveniently presented in unit dosage form, and prepared by any of the methods well known in the art of pharmacy.

The active compound can be combined with a pharmaceutical carrier according to conventional pharmaceutical compounding techniques. The carrier may take a wide variety of forms depending on the form of the preparation desired for administration, e.g. oral or parenteral (including intravenous injections or infusions). In preparing the compositions for oral dosage form any of the usual pharmaceutical media may be employed. Usual pharmaceutical media include, for example, water, glycols, oils, alcohols, flavoring agents, preservatives, coloring agents, and the like in the case of oral liquid preparations (such as for example, suspensions, solutions, emulsions and elixirs); aerosols; or carriers such as starches, sugars, micro-crystalline cellulose, diluents, granulating agents, lubricants, binders, disintegrating agents and the like, in the case of oral solid preparations (such as for example, powders, capsules, and tablets) with the oral solid preparations being preferred over the oral liquid preparations.

Another aspect of the present invention is to provide a method for the treatment or prevention of anxiety, epilepsy, sleep disorders, and insomnia, for inducing sedation-hypnosis, anesthesia, and muscle relaxation, and for modulating the necessary time to induce sleep and its duration in a human or non-human mammal, which comprises administering to said human or non-human mammal a therapeutically effective amount of the amorphous form together with one or more pharmaceutically acceptable carriers, excipients, diluents or adjuvants.

Because of their ease of administration, tablets and capsules represent the most advantageous oral dosage unit form, in which case solid pharmaceutical carriers are employed. If desired, tablets may be coated by standard aqueous or no aqueous techniques.

A suitable dosage range for use is from about 0.01 mg to about 100.00 mg total daily dose, given as a once daily administration or in divided doses if required.

Another aspect of the present invention is to provide the use of an amorphous form of compound (I) in the manufacture of a medicament for the treatment or prevention of anxiety, epilepsy, sleep disorders, and insomnia, for inducing sedation-hypnosis, anesthesia, and muscle relaxation, and for modulating the necessary time to induce sleep and its duration.

Amorphous compound (I) according to the present invention can be characterized by powder X-Ray Diffraction. The accompanying FIG. 1 shows a typical XR diffractogram, which is characterized by a broad halo, which is the characteristic feature of any amorphous material in X-Ray Diffraction.

The FT-Raman spectrum of amorphous compound (I), FIG. 2, exhibits the characteristic feature of broadened signals.

Like for the Raman spectrum, the ATR-IR spectrum of the amorphous material, FIG. 3, shows significantly broader signals than those of crystalline materials. A particularly intense absorption is found at 1099 cm$^{-1}$.

After in situ preparation, the amorphous form shows a Tg (glass transition temperature) of 61.3° C. However, the DSC curve of an aged amorphous sample, FIG. 4, shows a slightly higher Tg of 64° C. Above Tg the sample re-crystallized with an exothermic maximum at 117° C. and melted again at 167° C.

Like crystalline compound (I), the amorphous form is a potent ligand of $GABA_A$ and is useful in the treatment or prevention of anxiety, epilepsy, sleep disorders, and insomnia, for inducing sedation-hypnosis, anesthesia, and muscle relaxation, and for modulating the necessary time to induce sleep and its duration.

Figure 1:
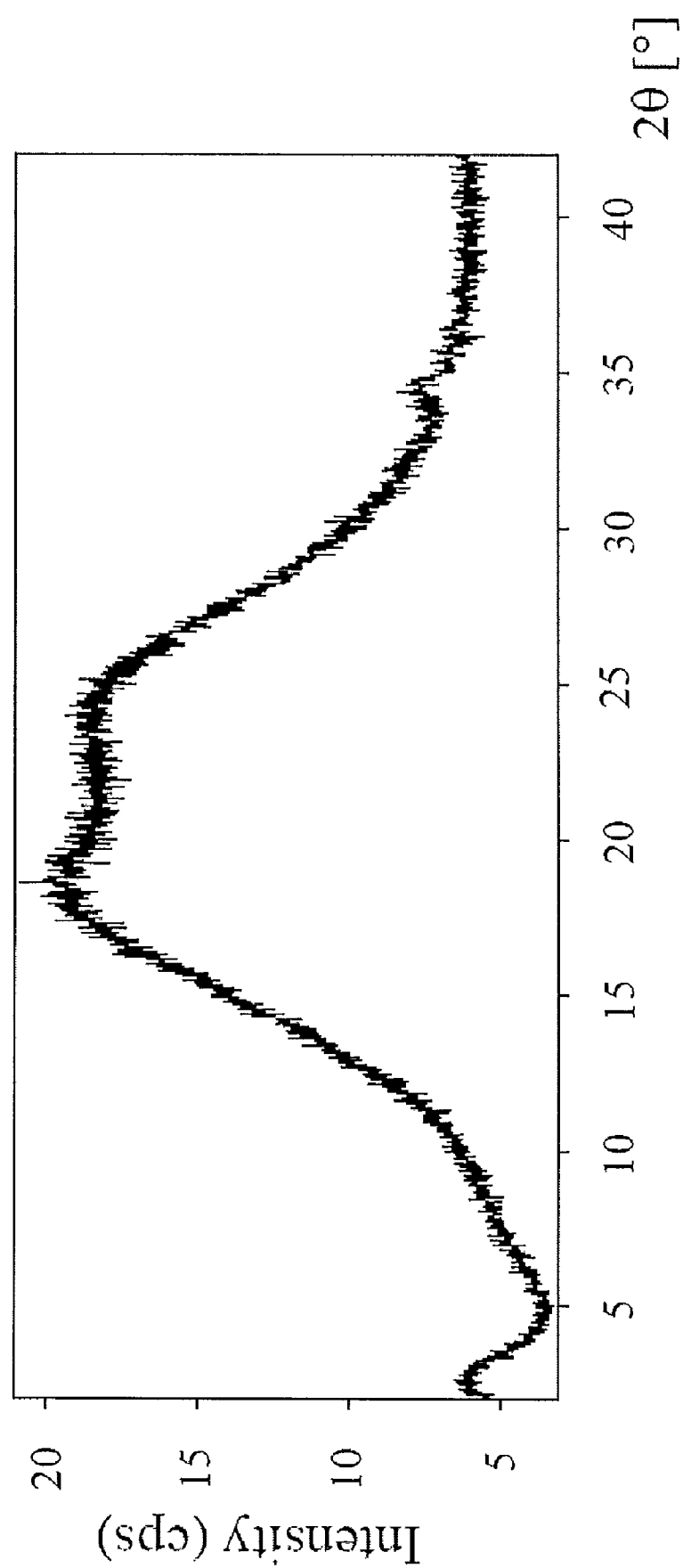
FIG. 1 is the Powder X-Ray Diffraction curve of compound (I) in amorphous form. The Intensity, on the ordinate, is expressed in cps.

In order that the invention may be more fully understood, the following examples are given by way of illustration only.

PREPARATION OF AN ANALYTICAL SAMPLE
(REFERENCE EXAMPLE)

Amorphous form of N-{2-Fluoro-5-[3-(thiophene-2-carbonyl)-pyrazolo[1,5-a]pyrimidin-7-yl]-phenyl}-N-methyl-acetamide N-{2-Fluoro-5-[3-(thiophene-2-carbonyl)-pyrazolo[1,5-a]pyrimidin-7-yl]phenyl}-N-methyl-acetamide (200 mg) was molten in an aluminum pan on a Kofler hot bench. The pan was removed after a couple of min and put on the cold bench top. The sample solidified within a few minutes and was slightly crushed in a mortar for analysis. The characteristics of the resulting product, comprising Powder X-Ray Diffraction, FT-Raman Spectroscopy, ATR-IR Spectroscopy, and DSC, are disclosed in the CHARACTERIZATION OF AMORPHOUS FORM section.

PREPARATIVE EXAMPLE

Amorphous form of N-{2-Fluoro-5-[3-(thiophene-2-carbonyl)-pyrazolo[1,5-a]pyrimidin-7-yl]-phenyl}-N-methyl-acetamide A 250 mL vessel was flushed with nitrogen and charged with 9.23 g (0.023 moles) of N-{2-Fluoro-5-[3-(thiophene-2-carbonyl)-pyrazolo[1,5-a]pyrimidin-7yl ]-phenyl}-N-methyl-acetamide and dichloromethane (92.3 mL, 10 volumes). The mixture was kept stirring to ensure complete dissolution, then charcoal (0.92 g) was added and the mixture warmed to 40° C. and agitated for at least 30 minutes. The suspension was cooled to 20-25° C. and the resulting mixture was filtered to remove charcoal, which was washed with further dichloromethane (2×18.5 mL). The dichloromethane extracts were merged and evaporated under vacuum and further dried under vacuum at 50° C. (±5° C.) to remove residual solvent. N-{2-Fluoro-5-[3-(thiophene-2-carbonyl)-pyrazolo [1,5-a]pyrimidin-7-yl]-phenyl}-N-methyl-acetamide was obtained as a solid (7.9 g) that was identified to be an amorphous material. Yield 85%. Purity ≧95%.

$^1$H NMR(400 MHz, CDCl$_3$): δ 1.98 (3H, s,), 3.3 (3H, s), 7.13 (1H, d, J=4Hz), 7.18-7.20 (1H, m), 7.42 (1H, t, J=8.8 Hz), 7.71 (1H, d, J=5.2 Hz), 8.02-8.08 (2H, m), 8.12 (1H, dd, J=2.4 and 7.6 Hz), 8.71 (1H, s), 8.82 (1H, d, J=4 Hz).

MS (ES) m/z=395 (MH$^+$)

The characteristics of the resulting product are fully concordant with those obtained in the reference example.

COMPOSITION EXAMPLE 1

5 mg Tablets

| | |
|---|---|
| Amorphous form of compound (I) | 5.0 mg |
| Colloidal silicon dioxide | 0.6 mg |
| Croscarmellose sodium | 12.0 mg |
| Talc | 4.0 mg |
| Magnesium stearate | 1.5 mg |
| Polysorbate 80 | 1.0 mg |
| Lactose | 75.0 mg |
| Hydroxypropyl methylcellulose | 3.0 mg |
| Polyethylene glycol 4000 | 0.5 mg |
| Titanium dioxide E171 | 1.5 mg |
| Microcrystalline cellulose q.s. to | 125.0 mg |

COMPOSITION EXAMPLE 2

10 mg Capsules

| | |
|---|---|
| Amorphous form of compound (I) | 70.0 mg |
| Colloidal silicon dioxide | 0.6 mg |
| Crospovidone | 12.0 mg |
| Talc | 4.0 mg |
| Magnesium stearate | 1.5 mg |
| Lauryl sulfate sodium | 1.5 mg |
| Lactose | 77.0 mg |
| Gelatin | 28.5 mg |
| Titanium dioxide E171 | 1.5 mg |
| Indigotin E132 | 0.02 mg |
| Microcrystalline cellulose q.s. to | 155.0 mg |

COMPOSITION EXAMPLE 3

Oral Drops

| | |
|---|---|
| Amorphous form of compound (I) | 0.5 g |
| Propylene glycol | 10.0 g |
| Glycerin | 5.0 g |
| Saccharin sodium | 0.1 g |
| Polysorbate 80 | 1.0 g |
| Lemon flavor | 0.2 g |
| Ethanol | 25.0 mL |
| Purified water q.s. to | 100.0 mL |

COMPOSITION EXAMPLE 4

2.5 mg Tablets

| | |
|---|---|
| Amorphous form of compound (I) | 2.5 mg |
| Colloidal silicon dioxide | 0.6 mg |
| Croscaramellose sodium | 12.0 mg |
| Talc | 4.0 mg |
| Magnesium stearate | 1.5 mg |
| Polysorbate 80 | 1.0 mg |
| Lactose | 75.0 mg |
| Hydroxypropyl methylcellulose | 3.0 mg |
| Polyethylene glycol 4000 | 0.5 mg |
| Titanium dioxide E171 | 1.5 mg |
| Microcrystalline cellulose q.s. to | 125.0 mg |

COMPOSITION EXAMPLE 5

5 mg Capsules

| | |
|---|---|
| Amorphous form of compound (I) | 5.0 mg |
| Colloidal silicon dioxide | 0.6 mg |
| Crospovidone | 12.0 mg |
| Talc | 4.0 mg |
| Magnesium stearate | 1.5 mg |
| Lauryl sulfate sodium | 1.5 mg |
| Lactose | 77.0 mg |
| Gelatin | 28.5 mg |
| Titanium dioxide E171 | 1.5 mg |
| Indigotin E132 | 0.02 mg |
| Microcrystalline q.s. to | 155.0 mg |

COMPOSITION EXAMPLE 6

Oral Drops

| | |
|---|---|
| Amorphous form of compound (I) | 0.25 g |
| Propylene glycol | 10.0 g |
| Glycerin | 5.0 g |
| Saccharin sodium | 0.1 g |
| Polysorbate 80 | 1.0 g |
| Lemon flavor | 0.2 g |
| Ethanol | 25.0 mL |
| Purified q.s. to | 100.0 mL |

Characterization of Amorphous Form

The amorphous form of compound (I) was characterized using the following procedures.

Instrumental and Experimental Conditions

Powder X-Ray Diffraction: Bruker D8 Advance. Cu Kα radiation; tube power 35 kV/45 mA; detector VANTEC1; 0.017° 2θ step size, 105±5 s per step, 2°-50° 2θ scanning range (printed range may be different). Silicon single crystal sample holders were used, sample diameter 12 mm, depth 0.1 mm.

FT-Raman Spectroscopy: Bruker RFS100. Nd:YAG 1064 nm excitation, 100 mW laser power, Ge-detector, 64 scans, range 50-3500 $cm^{-1}$, 2 $cm^{-1}$ resolution. Aluminum sample holder.

DSC: Perkin Elmer DSC 7. Gold crucibles, heating rates of 2° C. $min^{-1}$ or 10° C. $min^{-1}$, varying start and end temperatures.

Characteristics of Amorphous Form

Powder X-Ray Diffraction: The X-Ray diffractogram shows a broad halo, which is the characteristic feature of any amorphous material in X-ray diffraction. The X-Ray diffractogram is shown in FIG. 1. The Intensity, on the ordinate, is expressed in cps.

Figure 2:
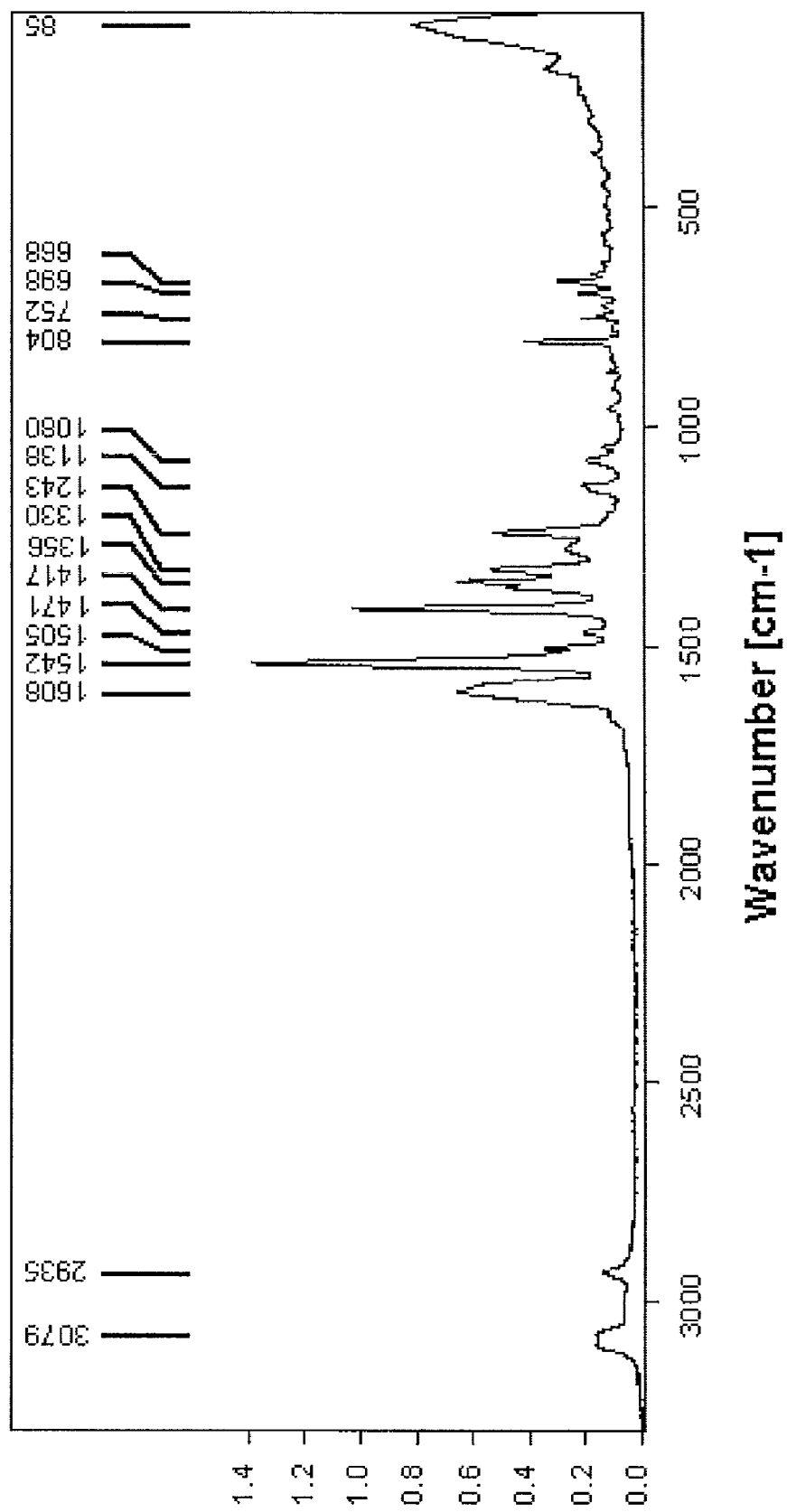
FIG. 2 is the Fourier-Transform (FT)—Raman Spectrum of compound (I) in amorphous form.

FT-Raman Spectroscopy: The FT-Raman spectrum is shown in FIG. 2.

Figure 3:
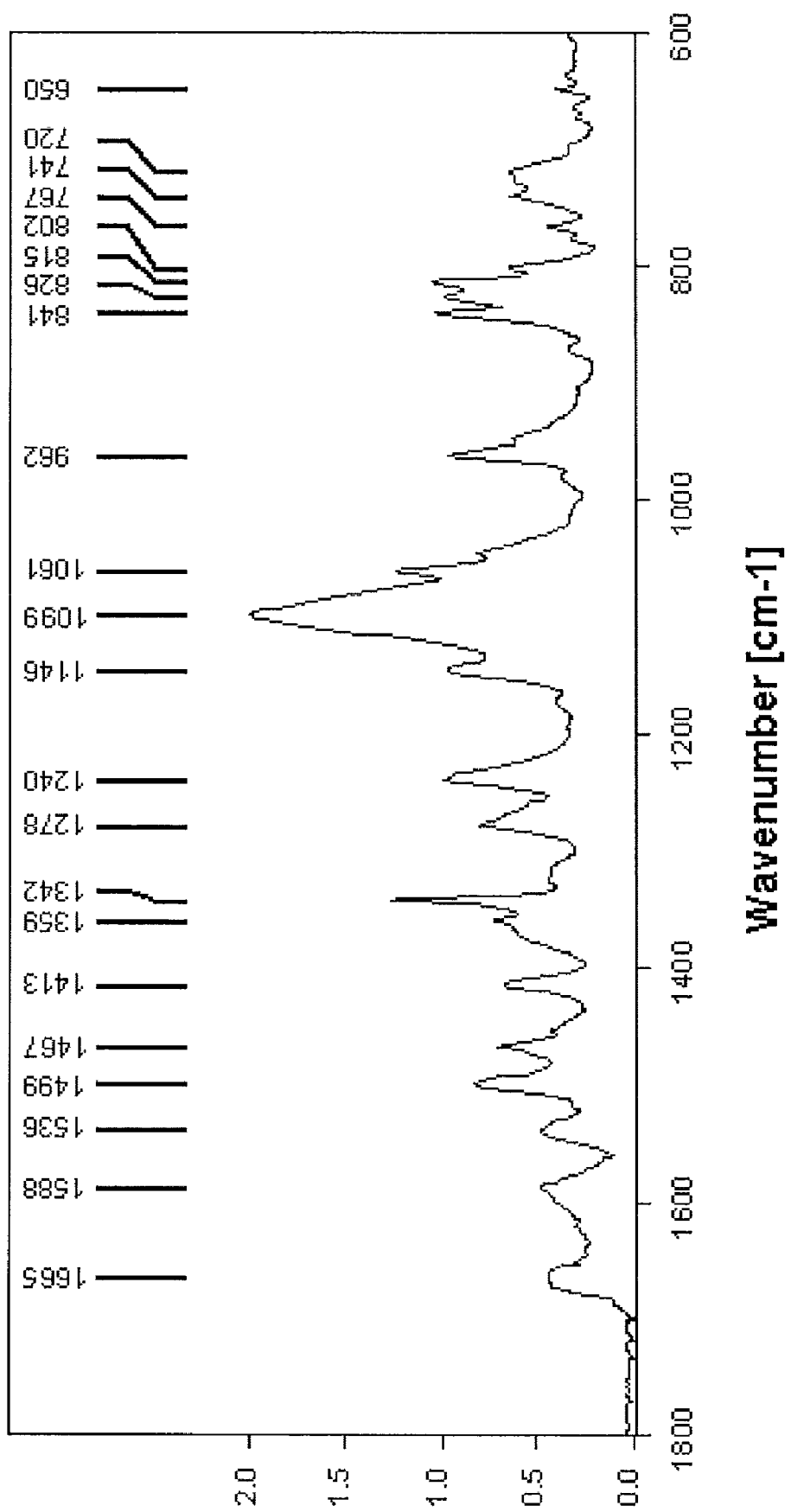
FIG. 3 is the Attenuated Total Reflection (ATR)—IR spectrum of compound (I) in amorphous form.

ATR-IR Spectroscopy: A particularly intense absorption is found at 1099 $cm^{-1}$. The ATR-IR spectrum is shown in FIG. 3.

Figure 4:
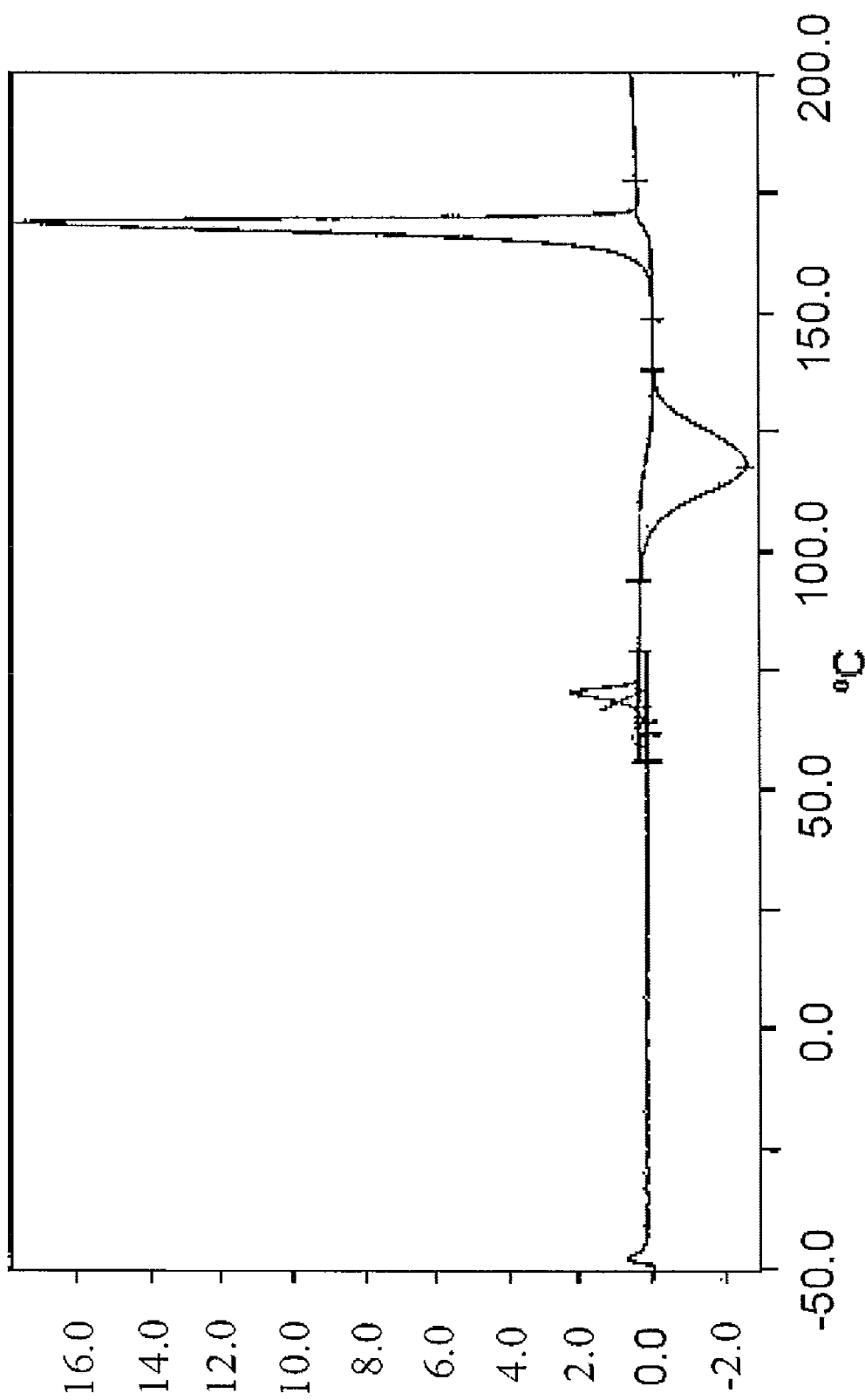
FIG. 4 is the Differential Scanning Calorimetry (DSC) curve of compound (I) in amorphous form.

DSC: After in situ preparation, the amorphous form showed a Tg of 61.3° C. The DSC curve of an aged amorphous sample showed a slightly higher Tg of 64° C. with a pronounced relaxation peak of about 7 J/g. Above Tg the sample re-crystallized with an exothermic maximum at 117° C. and melted again at 167° C. The melting temperature and melting enthalpy indicate that re-crystallization into crystalline material has taken place. It is noticeable that the re-crystallization enthalpy of 61 J/g to 67 J/g is more than 10% smaller than the melting enthalpy. This strongly suggests that some additional ordering existed already in the glassy state as compared to the melt above 167° C. One possible explanation could be that dimer formation has already taken place in the glassy "amorphous" state, but without any long-range ordering in the sample. The assumption of some ordering in the glassy state is corroborated by an evaluation of the ΔCp values. The ΔCp of the Tg amounts to 0.3 J/(g K) whereas it would typically be expected a value close to 0.4 J/(g K) for an amorphous low molar mass compound. Also, the ΔCp connected with the melting peak at 167° C. amounts to more than 0.4 J/(g K), and it is known that the ΔCp values at the melting peak and at the glass transition are typically very similar. From all this it has to be concluded that the so-called amorphous state contains a (pre)crystalline fraction that does not contribute to the glass transition and lowers the liberated re-crystallization energy. The DSC curve is shown in FIG. 4.

The invention claimed is:

1. A process for the preparation of an amorphous form of N-{2-Fluoro-5-[3-(thiophene-2-carbonyl)-pyrazolo[1,5-a]pyrimidin-7-yl]-phenyl}-N-methyl-acetamide, which process comprises:
    (a) dissolving N-{2-Fluoro-5-[3-(thiophene-2-carbonyl)-pyrazolo[1,5-a]pyrimidin-7-yl]-phenyl}-N-methyl-acetamide in dichloromethane;
    (b) evaporating the solvent under vacuum; and
    (c) drying the product to remove residual solvent.

2. A process for the preparation of an amorphous form of N-{2-Fluoro-5-[3-(thiophene-2-carbonyl)-pyrazolo [1,5-a] pyrimidin-7-yl]-phenyl}-N-methyl-acetamide, which process comprises:
- (a) dissolving N-{2-Fluoro-5-[3-(thiophene-2-carbonyl)-pyrazolo[1,5-a] pyrimidin-7-yl]-phenyl}-N-methyl-acetamide in dichloromethane;
- (b) evaporating the solvent under vacuum; and
- (c) drying the product to remove residual solvent, said process further comprises:
- (i) dissolving N-{2-Fluoro-5[3-(thiophene-2-carbonyl)-pyrazolo[1,5-a] pyrimidin-7-yl]-phenyl}-N-methyl-acetamide in dichloromethane;
- (ii) adding charcoal to the solution;
- (iii) warming the mixture to 30-50° C.;
- (iv) agitating the mixture for 20-45 minutes;
- (v) cooling the suspension to 15-30° C.;
- (vi) removing charcoal by filtration;
- (vii) evaporating the solvent under vacuum; and
- (viii) drying the product under vacuum at 40-60° C. to remove residual solvent.

3. The process according to claim 2 wherein the mixture in step (iii) is warmed to 40° C. (±5° C.).

4. The process according to claim 2 wherein the mixture is agitated in step (iv) for 30 minutes (±5 minutes).

5. The process according to claim 2 wherein the suspension in step (v) is cooled to 20-25° C.

6. The process according to claim 2 wherein the product in step (viii) is dried at 50° C. (±5° C.).

7. A method for treating anxiety, epilepsy, sleep disorders and insomnia, for inducing sedation-hypnosis, anesthesia and muscle relaxation, and for modulating the necessary time to induce sleep and its duration, which comprises administering an amorphous form of N-{2-Fluoro-5-[3-(thiophene-2-carbonyl)-pyrazolo[1,5-a] pyrimidin-7-yl]-phenyl}-N-methyl-acetamide to a patient in need thereof.

8. A method for treating anxiety, epilepsy, sleep disorders and insomnia, for inducing sedation-hypnosis, anesthesia and muscle relaxation, and for modulating the necessary time to induce sleep and its duration, which comprises administering a medicament which comprises the amorphous form of N-{2-Fluoro-5-[3-(thiophene-2-carbonyl)-pyrazo[1,5-a]pyrimidin-7-yl]-phenyl}-N-methyl-cetamide to a patient in need thereof.

* * * * *